(12) United States Patent
Nabai

(10) Patent No.: US 11,311,063 B2
(45) Date of Patent: Apr. 26, 2022

(54) LOUPE LIGHT-COMPATIBLE ATTACHABLE FACE SHIELD

(71) Applicant: LoupeSaver, LLC, Del Mar, CA (US)

(72) Inventor: Sarah Nabai, Palo Alto, CA (US)

(73) Assignee: LoupeSaver, LLC, Del Mar, CA (US)

( * ) Notice: Subject to any disclaimer, the term of this patent is extended or adjusted under 35 U.S.C. 154(b) by 41 days.

(21) Appl. No.: 16/738,877

(22) Filed: Jan. 9, 2020

(65) Prior Publication Data

US 2020/0253301 A1 Aug. 13, 2020

Related U.S. Application Data

(63) Continuation of application No. 15/234,931, filed on Aug. 11, 2016, now abandoned, which is a continuation-in-part of application No. 14/062,801, filed on Oct. 24, 2013, now Pat. No. 10,231,495.

(60) Provisional application No. 61/718,058, filed on Oct. 24, 2012.

(51) Int. Cl.
| | |
|---|---|
| *A61F 9/00* | (2006.01) |
| *A41D 13/11* | (2006.01) |
| *A61B 90/35* | (2016.01) |
| *A61F 9/02* | (2006.01) |
| *A61B 90/00* | (2016.01) |
| *A61B 90/30* | (2016.01) |
| *A61B 90/50* | (2016.01) |

(52) U.S. Cl.
CPC .......... *A41D 13/1184* (2013.01); *A61B 90/05* (2016.02); *A61B 90/30* (2016.02); *A61B 90/35* (2016.02); *A61F 9/022* (2013.01); *A61F 9/029* (2013.01); *A61B 2090/502* (2016.02)

(58) Field of Classification Search
CPC ..... A41D 13/1184; A61B 90/05; A61B 90/30; A61B 90/35; G02C 11/12; G02C 7/16; G02C 11/00; G02C 9/04; A61F 9/022; A61F 9/045; A61F 9/04; A61F 9/00; A61F 9/02; A61F 9/029
USPC ......................................................... 128/858
See application file for complete search history.

(56) References Cited

U.S. PATENT DOCUMENTS

| | | |
|---|---|---|
| 2,765,789 A | 10/1956 | Schmierer |
| 2,881,443 A | 4/1959 | Barker, Jr. |
| 2,762,050 A | 9/1965 | Bricker |
| 3,310,812 A | 3/1967 | Gaisser |
| 3,328,806 A | 7/1967 | Allegro |
| 4,323,063 A | 4/1982 | Fisichella |
| 4,837,862 A | 6/1989 | Heil |
| 4,856,509 A | 8/1989 | Lemelson |
| 4,920,960 A | 5/1990 | Hubbard et al. |
| 4,944,294 A | 7/1990 | Borek |
| 5,020,533 A | 6/1991 | Hubbard et al. |
| D355,715 S | 2/1995 | Hubbard et al. |
| 5,682,879 A | 11/1997 | Bowers |
| 5,813,398 A | 9/1998 | Baird et al. |

(Continued)

*Primary Examiner* — Victoria H Fisher
(74) *Attorney, Agent, or Firm* — Shay Glenn LLP

(57) ABSTRACT

A face shield adapted to protect the face from biohazards during medical procedures is disclosed. The central portion of the face shield includes a horizontally centered cut out that extends downwardly from a top edge. The cut out is sized and positioned to allow a loupe light to pass through. The central portion of the face shield may be hingedly connected to a pair of side portions. A pair of side portions extends outwardly from respective sides of the central portion. Each of the pair of side portions includes attachment structure, such as a clip, to attach the face shield to the temples of a pair of loupes.

29 Claims, 8 Drawing Sheets

(56) References Cited

U.S. PATENT DOCUMENTS

| | | |
|---|---|---|
| 6,026,511 A | 2/2000 | Baumann et al. |
| D440,652 S | 4/2001 | Pollard |
| 6,213,125 B1 | 4/2001 | Reese et al. |
| 6,698,427 B1 | 3/2004 | Clowers |
| D530,418 S | 10/2006 | Henry et al. |
| 7,191,778 B2 | 3/2007 | Shue et al. |
| 7,681,256 B2 | 3/2010 | Fullerton et al. |
| 7,992,558 B2 | 8/2011 | Thornton et al. |
| 8,020,276 B2 | 9/2011 | Thornton |
| 8,051,855 B2 | 11/2011 | Ho et al. |
| 10,231,495 B2 | 3/2019 | Nabai |
| 2011/0179540 A1 | 7/2011 | Sutton |
| 2011/0203594 A1 | 8/2011 | Brain |
| 2011/0239347 A1 | 10/2011 | Beliveau |
| 2016/0353815 A1 | 12/2016 | Nabai |

LOUPE LIGHT-COMPATIBLE ATTACHABLE FACE SHIELD

CROSS REFERENCE TO RELATED APPLICATIONS

This application is a continuation of U.S. patent application Ser. No. 15/234,931, filed Aug. 11, 2016, which is a continuation-in-part of U.S. patent application Ser. No. 14/062,801, filed Oct. 24, 2013, which claims priority to U.S. Provisional Patent Application No. 61/718,058, filed Oct. 24, 2012. Each of those applications are incorporated by reference in their entirety.

BACKGROUND OF THE INVENTION

1. Field of the Invention

The invention relates to disposable body substance isolation equipment, and in particular, to medical masks with eye shields that are compatible with loupe lights.

2. Description of Related Art

Over the last several decades, both medical professionals and the general public have become far more aware of the dangers of pathogens in bodily fluids. Some of the pathogens themselves have become increasingly virulent, and drug resistance has become an issue with strains of bacteria that were once easily eradicated using standard antibiotics.

Products that are intended to prevent a medical practitioner from coming into contact with potentially infectious bodily fluids are referred to generally as body substance isolation (BSI) equipment. One of the most common types of BSI equipment is the face mask.

Face masks exist in several forms, perhaps the most common of which is the filter mask. A filter mask is essentially a piece of material that is worn over the nose and mouth to filter the incoming and outgoing breath, thus preventing the wearer from being infected by others and others from being infected by the wearer. The filter mask is typically tied around the back of the head and neck, or includes elastic straps that are looped over the ears. Surgeons typically wear this kind of face mask during most surgical procedures, and some patients with chronic conditions, like tuberculosis, may routinely wear filter masks to prevent others from becoming infected.

Filter masks may be adequate for some applications where small droplets in the breath are the primary concern. However, for applications in which blood and other bodily fluids may splash or splatter, full-face protection may be more desirable. For example, full-face protection is becoming increasingly common in dental offices, where the dentist or hygienist has close contact with the patient.

There are several common options for full-face protection. The first, and perhaps most complete, is a helmet-style shield that fits over the head and covers the face entirely. In some versions, the face shield portion may rotate up and out of the way when not needed. Although effective and able to offer full wrap-around protection of the head and face, this equipment is cumbersome, and can be hot and uncomfortable to wear.

A second, lighter option is a filter mask with an integrated plastic face shield. In masks of this sort, a clear piece of plastic is attached to and around the filter mask and extends upwardly to cover the face. While useful, and often more comfortable than a helmet-style shield, these disposable integrated face shields often do not have good wrap-around coverage of the face, i.e., they may offer poor protection for the side of the face and are not contoured to fit the face well.

Another problem with the standard disposable integrated face shield is that medical providers often wear glasses or other equipment on their faces. For example, it is extremely common for a medical provider to wear a set of loupes. Loupes bear a general resemblance to glasses, and typically include magnifiers (2.5.times. and 3.5.times. are common magnifications) as well as a light. When worn, a loupe light is typically centered on the brow, just above the bridge of the nose. Unfortunately, standard disposable face shields cannot accommodate this kind of equipment, which projects out from the face.

SUMMARY OF THE INVENTION

One aspect of the invention relates to a face mask. The face mask has a filter mask portion with an attached face shield portion and is adapted to be compatible with loupes and a loupe light. Specifically, the central portion of the face shield includes an essentially horizontally centered cut out that extends downwardly from a top edge. The cut out is sized and positioned to allow a loupe light to pass through. The central portion of the face shield is hingedly connected to a pair of side portions. The side portions may include openings that allow straps from the filter mask to pass through and secure the side portions against the head. In some embodiments, the central portion may include a frangible section that can be removed to create the cut out.

Another aspect of the invention relates to a face shield. The face shield comprises a thin, transparent sheet of material with a central portion connected to two side portions. The central portion includes an essentially horizontally centered cut out that extends downwardly from a top edge. The cut out is more vertical than horizontal, such that the width is at most equal to the height or depth of the cut out. Each of the side portions includes attachment structure, such as a clip, that is adapted to attach the face shield to one of the temples of a pair of loupes. In some embodiments according to this aspect of the invention, a fold or score line may separate the central portion from the side portion, allowing the side portions to fold relative to the central portion.

A further aspect of the invention relates to a face shield. The face shield comprises a thin, transparent sheet of material with a central portion connected to two side portions. The central portion includes an opening essentially horizontally centered on the central portion and positioned vertically some distance down from a top edge of the central portion. The opening is sized to admit a loupe light. Each of the side portions includes attachment structure, such as a clip, that is adapted to attach the face shield to one of the temples of a pair of loupes. In some embodiments according to this aspect of the invention, a fold or score line may separate the central portion from the side portion, allowing the side portions to fold relative to the central portion.

These and other aspects, features, and advantages of the invention will be described below.

BRIEF DESCRIPTION OF THE DRAWING FIGURES

The invention will be described with respect to the following drawing figures, in which like numerals represent like features throughout the drawings, and in which.

DETAILED DESCRIPTION

Figure 1:
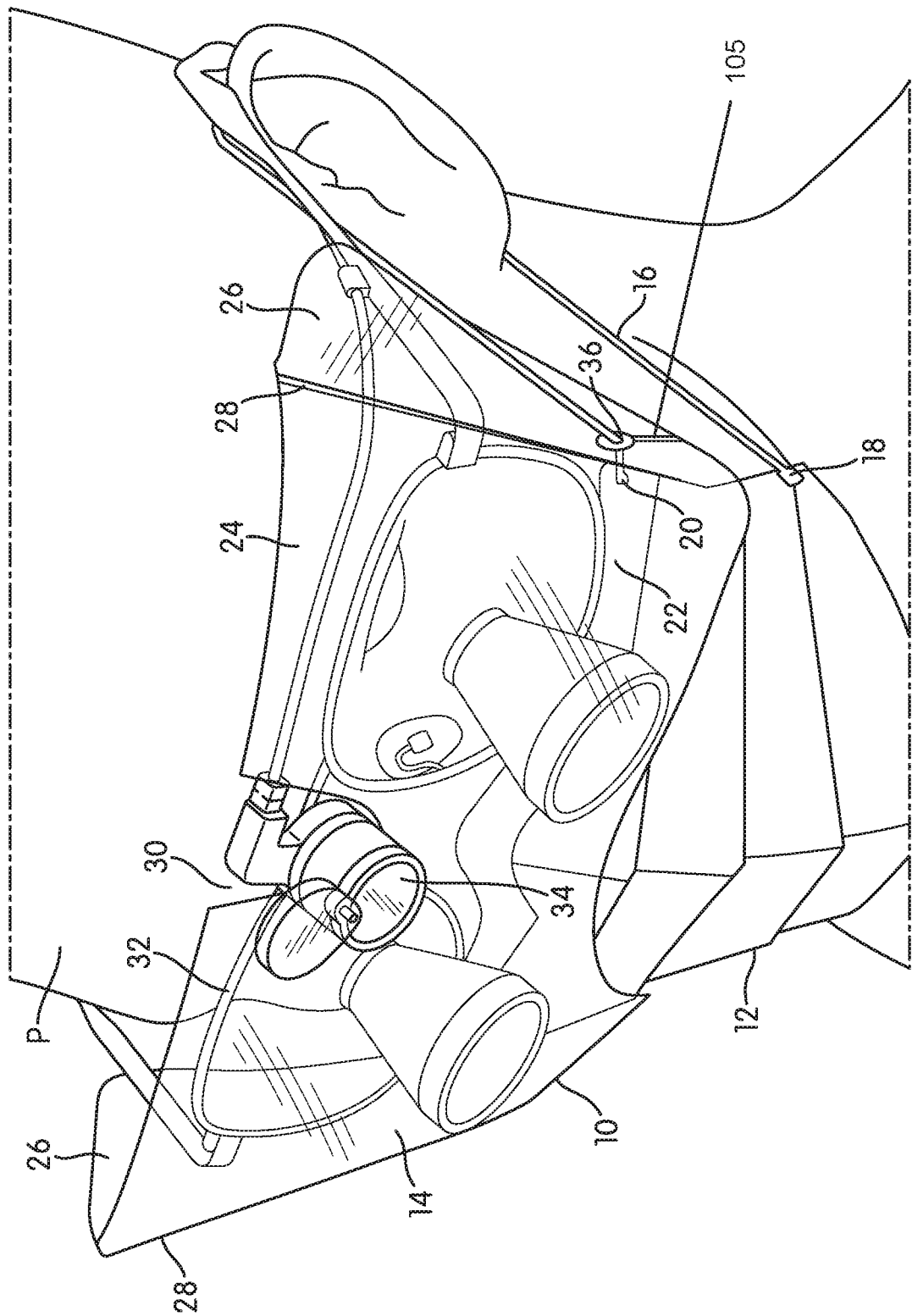
FIG. 1 is a perspective view of a medical mask with a loupe light-compatible eye shield according to one embodiment of the invention.

FIG. 1 is a perspective view of a medical mask with a loupe light-compatible eye shield, generally indicated at 10, according to one embodiment of the invention, shown as worn on the head of a person P. The medical mask 10 includes both a filter mask portion 12 and a face shield portion 14.

The filter mask portion 12 is a pleated sheet of natural or polymer fibers that is extended over the nose and the mouth, down to and beyond the level of the chin. The construction of filter masks is well known in the art, and any known materials may be used for the filter mask portion 12. The material of which the filter mask portion 12 is made may depend on any number of factors, including the size of particulate or aerosol matter that the filter mask portion 12 is intended to filter. In the illustrated embodiment, the medical mask 10 and filter mask portion 12 are secured by a pair of elastic straps 16, each of which is secured to the filter mask portion 12 at two locations 18, 20. Depending on the embodiment, the straps 16 may be sewn or fused to the filter mask portion 12, or simply passed through it and knotted. Of course, inextensible tied straps or other methods of securement may be used instead of elastic straps 16.

Provided above the filter mask portion 12 and covering the eyes, brow, and sides of the face in FIG. 1 is the face shield portion 14. The face shield portion 14 is attached at its left and right edges to the left and right edges of the filter mask portion 12, typically by fusing, adhesives, or any other known means. The bottom edge of the face shield portion 14 is typically free to move relative to the filter mask portion 12, and an upper strip 22 of the filter mask portion 12 includes an embedded malleable metal strip that can be contoured to fit the nose. As shown, there is some overlap between the filter mask portion 12 and the face shield portion 14; the face shield portion 14 extends below the top of the filter mask portion 12 and terminates in a concave curve with a high point proximate to the tip of the nose, which helps to accommodate the nose. Of course, the bottom curvature of the filter mask portion 12 may vary from embodiment to embodiment, and in some embodiments, the filter mask portion 12 may be squared off.

The face shield portion 14 itself is made from a thin, transparent sheet of material, and includes a central portion 24 and two side portions 26. The side portions 26 are connected to the central portion 24 by respective hinges 28, which may, for example, be living hinges or scores that allow the two side portions 26 to fold and bend relative to the central portion 24. This, in turn, may allow better coverage of the sides of the face as compared with conventional face masks, in which there are no hinges and the plastic simply wraps around the face as best it can. The hinges 28 may also reduce the tendency for the face shield portion 14 to warp, crimp, or distort, which may interfere with the provider's view or be uncomfortable.

Additionally, the central portion 24 of the face shield portion 14 defines a cut out 30. The cut out 30 is essentially horizontally centered on the face shield portion 14, and extends downwardly from a top edge of the face shield portion 14. As shown in FIG. 1, when a user is wearing loupes 32 with a loupe light 34, the cut out 30 allows the loupe light 34 to pass through the face shield portion 14, thus making it easier to wear loupes 32, a loupe light 34, and the mask 10 at the same time.

The cut out 30 of the illustrated embodiment is wider at the top and narrower at the bottom, and the bottom may be rounded (i.e., to match or approximate the curvature of a typical loupe light 34). The shape of the cut out 30 may be different in other embodiments—for example, the bottom may be squared, and the top may have a different taper or no taper at all. In one embodiment, for example, the cut out 30 may be about 2.5 inches at its top, about 2 inches at its bottom, and with a height of about 2.5 inches, which provides enough room to accommodate a typical loupe light 34. However, other embodiments may use different dimensions, and as was noted above, the cut out 30 need not taper in all embodiments. In other words, the cut out 30 may have straight sides and a rounded bottom or straight sides and a squared-off bottom.

While the sidewalls of the cut out 30 are completely straight in the illustrated embodiment, that need not be the case in all embodiments. The sidewalls may instead have curvature of various types, either continuous or discontinuous. In other words, the sidewalls may be only substantially—but not completely—straight, or they may not be straight at all. However, a straight-sided cut out 30 may be easier to manufacture.

As a general matter, it is advantageous if the cut out 30 has the minimum dimensions necessary to admit the loupe light 34. Put another way, it is advantageous if the cut out 30 admits the loupe light 34 but otherwise compromises the protective function of the face shield portion 14 as little as possible. As can be appreciated from the figures, the cut out 30 is more vertical than horizontal. Put another way, the width is typically at most equal to the depth, and in many cases, the cut out 30 may be deeper than it is wide.

In some embodiments, masks 10 may be made with no cut out 30. In other embodiments, masks may be made with a perforated frangible portion that can be torn off to create a cut out like the cut out 30 illustrated in FIG. 1. Of course, the user is under no obligation to remove a frangible portion if one is present, and may use a face mask without removing a frangible portion if, for example, he or she does not wish to wear a loupe light 34.

In embodiments of the invention, the straps 16 or ties that secure the mask 10 to its wearer may cooperate with the side portions 26 to secure them around the sides of the face or otherwise maintain their position, creating a wrap-around effect.

As shown in FIG. 1, the top half of each elastic strap 16 passes through a hole 36 defined toward the bottom of the side portion 26, emerges on the outside of the side portion 26 and, because of the tension in it, presses against the side portion 26 and keeps it against the face as the strap 16 extends toward and around the ear.

Figure 2:
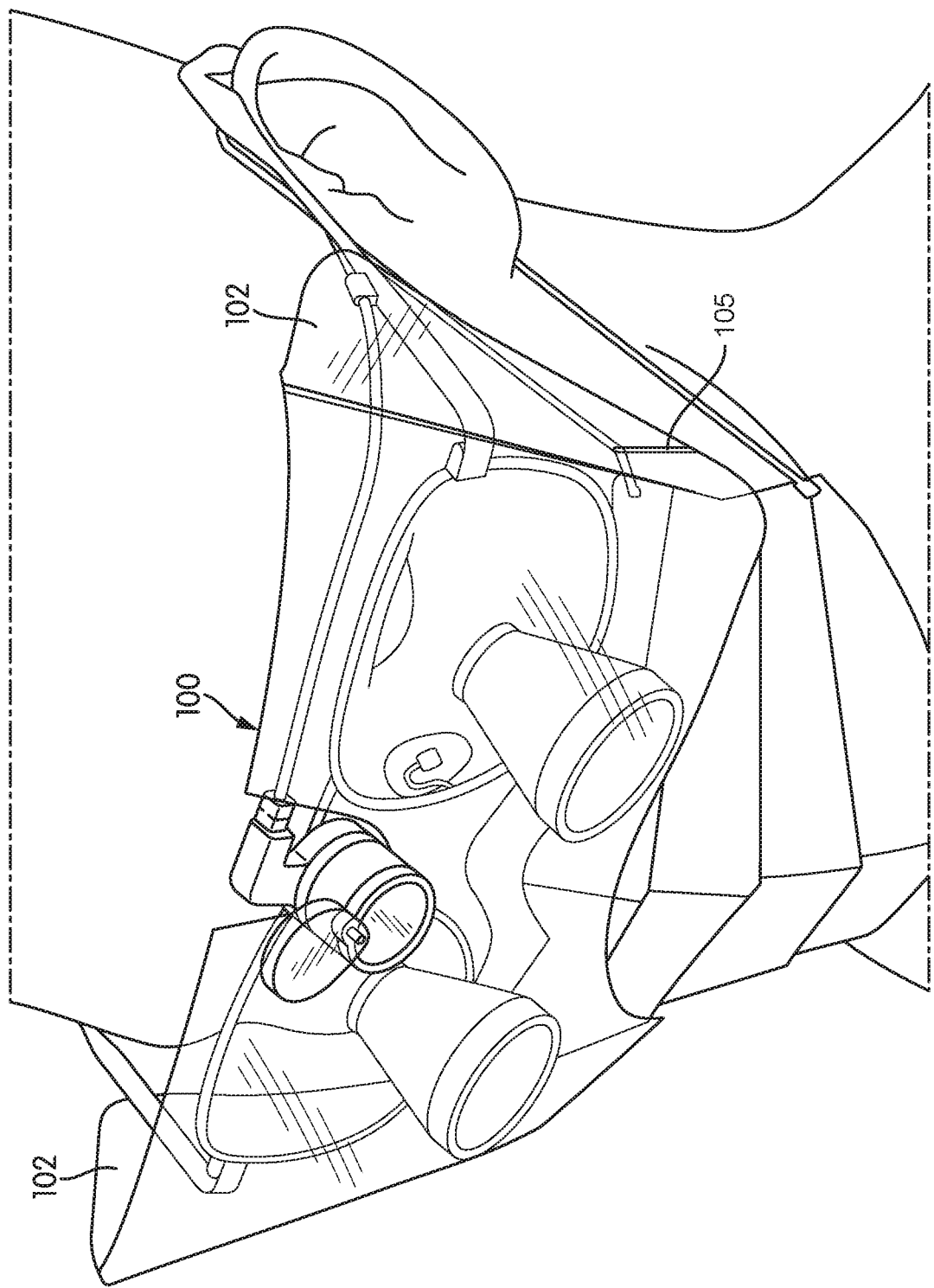
FIG. 2 is a perspective view of a medical mask according to another embodiment of the invention.

Each hole 36 may be reinforced, for example, by an additional layer or layers of plastic fused or sintered around each hole 36. However, the holes 36 need not be reinforced. In fact, the side portion 26 need not have a hole 36 per se; instead, any kind of opening of sufficient size to allow the strap 16 to pass may be used. As one example, FIG. 2 is a perspective view similar to the view of FIG. 1 illustrating another embodiment of the invention, generally indicated at 100. The face mask 100 has essentially the same features as the mask 10 described above. However, in each side portion 102, a slit 104 extends from the bottom edge up. The slit 105 has an upward most point at about the same position where a hole 36 would be in mask 10. In some embodiments, the slit 105 may terminate in a hole, although it need not. In some embodiments, there may be no opening in the side portion 26, 102 at all.

Figure 3:
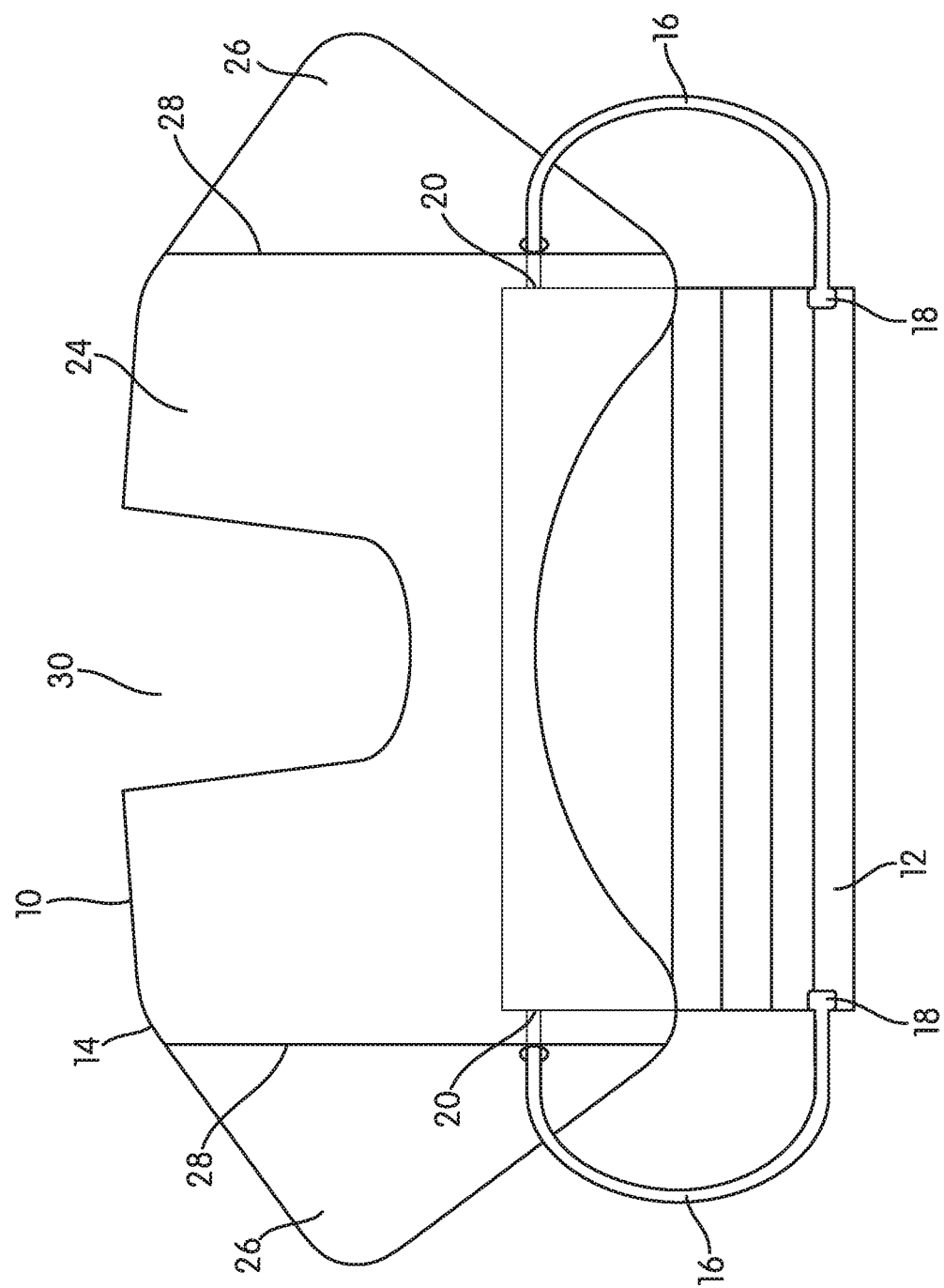
FIG. 3 is a front elevational view of the mask of FIG. 1.

FIG. 3 is a front elevational view of the mask 10 of FIG. 1, illustrating how the mask 10 appears when not in use. One advantage of the mask 10 is that when not in use, it is essentially flat, making it easier to package and ship. However, it should be understood that although the filter mask portion 12 of the illustrated embodiment is a pleated flexible material that contours to the face, in other embodiments, the filter mask portion could be a dome-shaped mask with sufficient rigidity to hold its own shape. Masks of this type are known, and are often used to filter dust and other particulate matter.

While the mask 10 provides comprehensive protection, with integrated filter mask and face shield portions 12, 14, there are cases in which it may be advantageous for the two components to be separate. For example, this would allow the wearer to use a different style or type of mask, like a dome-shaped mask, and to tie off that mask in a different way than an integrated mask 10 would allow.

Figure 4:
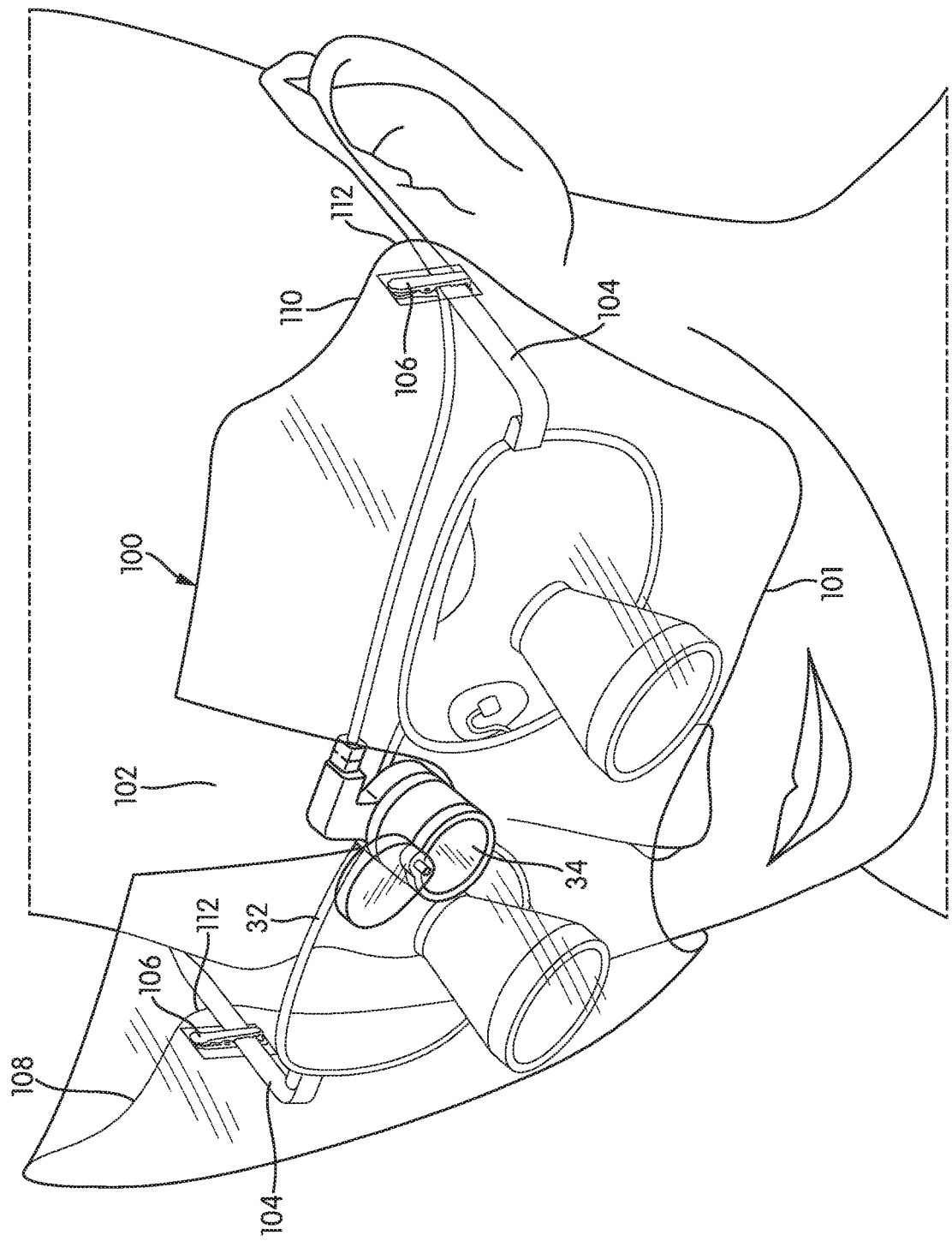
FIG. 4 is a perspective view of an attachable face shield according to another embodiment of the invention.

FIG. 4 is a perspective view of a face shield, generally indicated at 100, according to another embodiment of the invention. The face shield 100, like the face shield portion 14, comprises a thin, relatively flexible sheet of plastic. Typically, the face shield 100 has enough rigidity to hold the shape shown in FIG. 4, but is also flexible, as will be described below in more detail. For example, the face shield portion 14 may be 4 mil (0.1 mm) polyethylene terephthalate (PET). In embodiments of the invention, the face shield portion 14 and face shield 100 may be PET, polycarbonate, or another such transparent, durable material.

While much of this description may assume that the face shield 100, like the face shield portion 14, is transparent and clear, in some cases, shields 14, 100 may be made in other colors or with particular light-blocking properties. For example, dentists often use UV-curing adhesives in procedures, and a face shield 100 could be a UV filter, in which case, it would typically appear orange. In some cases, only the portion of the face shield 100 that lies over the eyes need have UV-filtering capabilities. In that case, a UV-filtering strip could be applied to the face shield with adhesives or by fusing the two layers together at manufacture.

As shown in FIG. 4, when in use, the face shield 100 extends from a line along the forehead down to the cheeks but, as in the previous embodiment, sweeps upward with a concavely curved lower edge 101, terminating at its highest point just above the point of the nose. Thus, the face shield 100 protects roughly the same area as the face shield portion 14, although it may extend farther up along the forehead, if desired or necessary. As those of skill in the art will appreciate, the face shield 100 may be made in different sizes, if necessary, to maintain the same coverage areas for people with differently sized or shaped faces.

The face shield 100 is constructed and adapted to protect a user wearing loupes 32 with a loupe light 34, and to allow the loupe light 34 to pass through. As with the face shield portion 14, the face shield 100 has a cut out 102. The cut out 102 has the same general features as the cut out 30 described above, although if the face shield 100 extends farther up along the forehead, the cut out 102 may be deeper than the cut out 30 of the face shield portion 14. The dimensions of the cut out 102 will be described in greater detail below.

Compared with the integrated mask 10 described above, the face shield 100 is held in place in an entirely different way: it attaches releasably to the temples 104 of the loupes 32. In the illustrated embodiment, two small clips 106 are fastened to the inner side of the face shield 100 near its left and right edges. The clips 106 are alligator clips—they are spring-loaded with serrated jaws. However, other forms of clips and attachment hardware may be used. Because of the clips 106, the face shield 100 does not need to be attached around the ears or around the circumference of the head, which may make for more comfortable wear by the user. As can be seen in the figures, no straps are provided.

Although one clip 106 is used on each side of the face shield 100 in the illustrated embodiment, more than one clip 106 may be used on each side if necessary or desirable for stability. Alternatively, the clip 106 or other method of securement may make contact over a wider area of each temple 104. For example, instead of clips 106, hook-and-loop fastener or adhesive tape may be used, and those methods would typically involve coverage over a wider area. Small elastic bands may also be used to attach the face shield 100 to the temples 104.

As can be seen in FIG. 4, the side portions 108, 110 that carry the clips 106 taper along the top and bottom edges and terminate at broad, rounded points 112 midway along the temples 104 of the loupes 32, giving them a concave triangular shape. The clips 106 are mounted just inward of those points 112. As can also be seen in FIG. 4, the side portions 108, 110 are contiguous with the rest of the face shield 100—there is no break or dividing line between them. In essence, the face shield 100 is flexible, and is simply bent around the loupes 32 and secured to the temples 104 with the clips.

Figure 5:
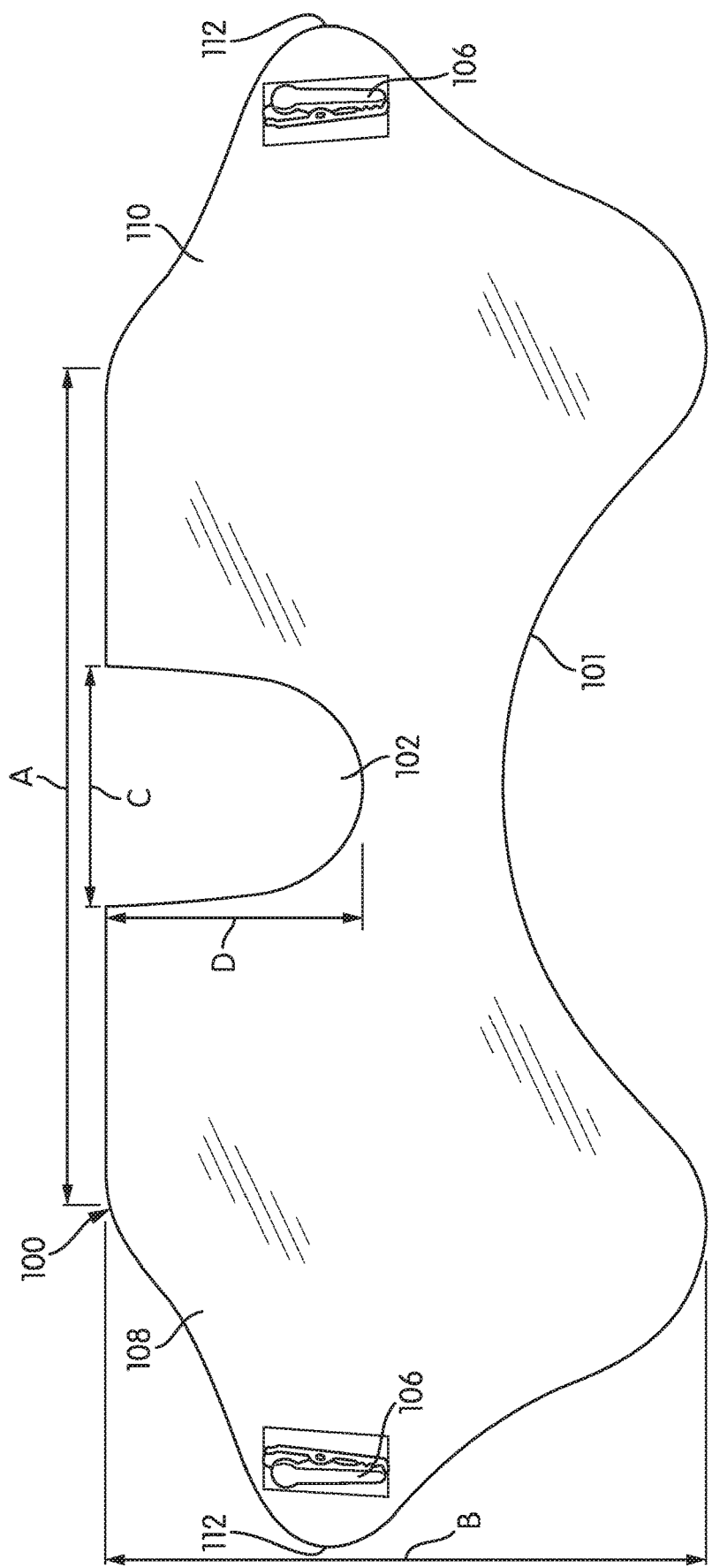
FIG. 5 is a top plan view of the attachable face shield of FIG. 4 shown in isolation.

FIG. 5 is a top plan view of the face shield 100 in isolation, showing its dimensions. In particular, the face shield 100 has a main width, identified in FIG. 5 as A, excluding the side portions 108, 110, of about 7 inches, and a maximum height, identified in FIG. 5 as B, of about 5 inches. In this embodiment, the cut out 102 has a maximum height, C, of 2.5 inches and a maximum width at the top along the top edge, D, of 2.125 inches, and a maximum height or depth, D, of 2.5 inches. The side portions 108, 110 may be, for example, about 3 inches measured along a side from the point of maximum height to the point 112. Thus, the cut out 102 of the face shield 100 is, like its counterpart described above, deeper than it is wide.

Figure 6:
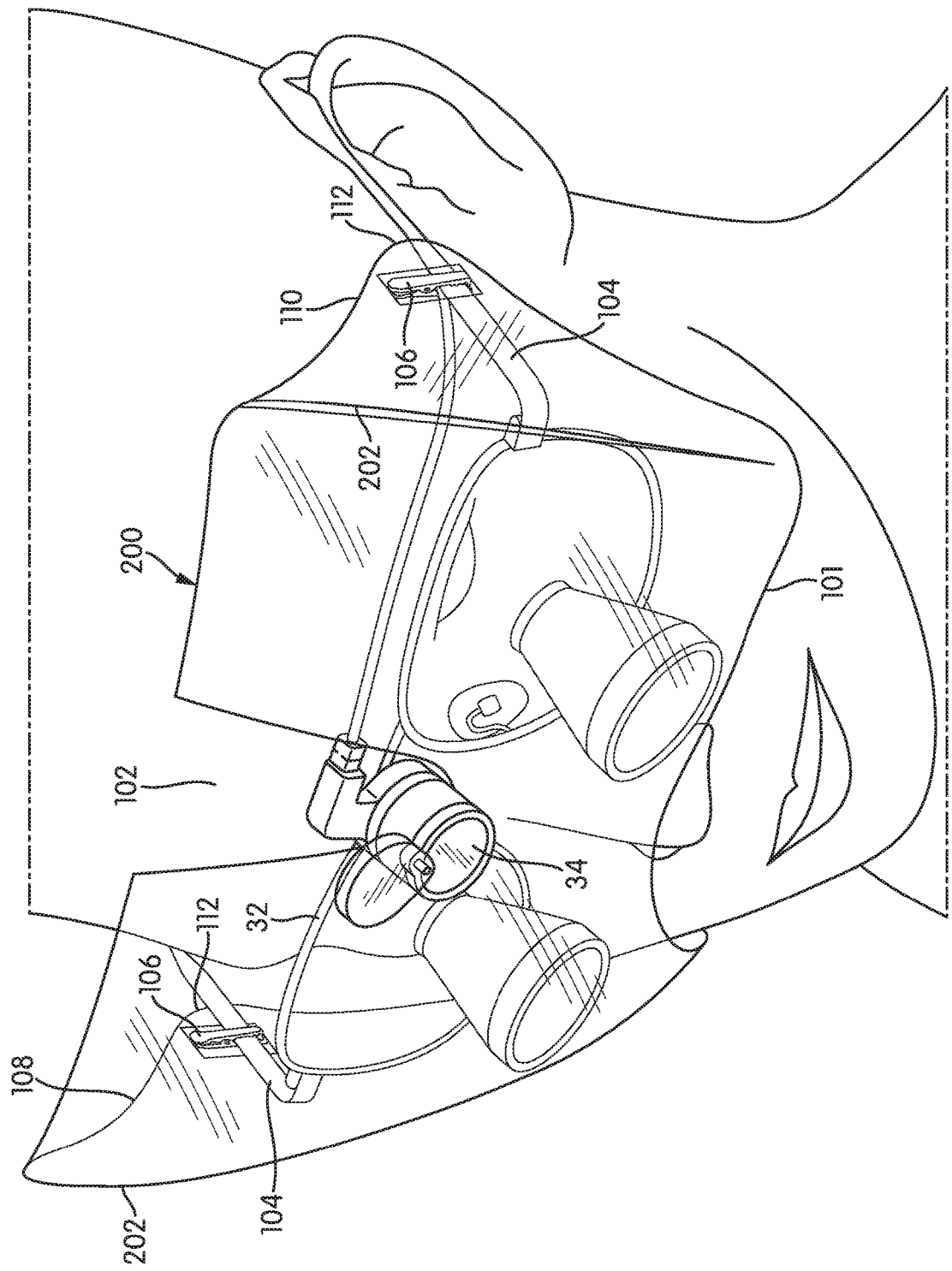
FIG. 6 is a perspective view of an attachable face shield according to yet another embodiment of the invention.

As was noted above, in the embodiment of FIGS. 4-5, the face shield 100 simply bends around the loupes 32 and is secured to the temples 104. That need not always be the case. FIG. 6 is a perspective view of another embodiment of a face shield, generally indicated at 200. The face shield 200 has features very similar to the features of the face shield 100, thus, except as noted, the description above applies to both face shields 100, 200. As compared to the face shield 100, the face shield 200 has score or fold lines 202 that divide the side portions 108, 110 from the rest of the face shield 200 and allow them to fold against the loupes 34. The face shield 200 with its fold lines 202 may be particularly useful in cases where it is necessary or desirable to make the face shield 200 thicker, for example, to hold its shape when large amounts of spatter or projectile contaminants are expected. There is no particular upper limit on the thickness of the face shields 100, 200, particularly if fold lines 202 are used, so long as the face shields 100, 200 are not so heavy that the loupes 32 shift position or slide down the nose.

Although FIGS. 4-6 illustrate the clips 106 attaching the face shields 100, 200 to the temples 104 of the loupes 32 at particular positions, any positions may be used. Typically, the user will select an attachment position that feels most comfortable and places the face shield 100, 200 as far forward as it needs to be to accommodate magnifiers and other features of the loupes 32.

Figure 8:
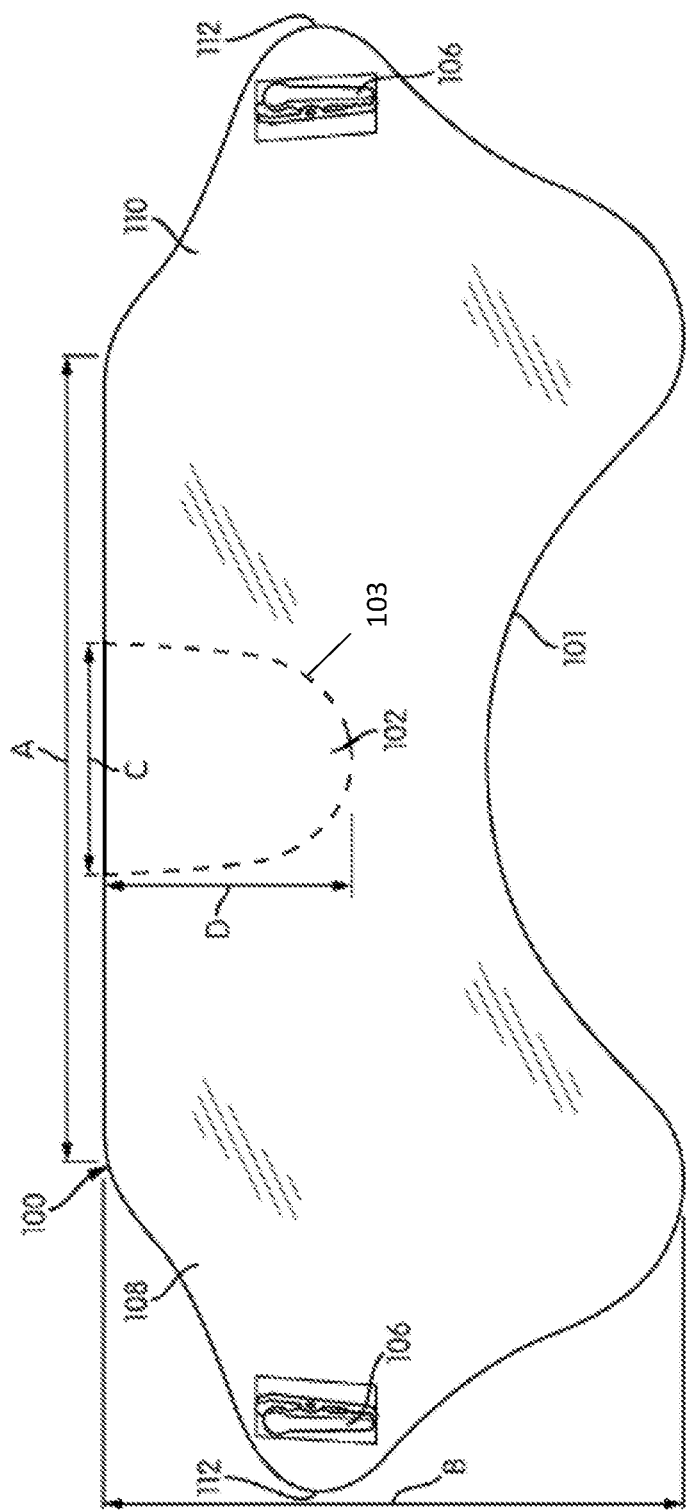
FIG. 8 is a top plan view of the attachable face shield of FIG. 5 showing a frangible cut out.

Additionally, while FIGS. 4-6 illustrate the face shields 100, 200 with cut outs 102, in some embodiments, as with the face shield portion 14, the face shields 100, 200 may have frangible portions 105 that can be torn out to form cut outs 102, rather than cut outs 102 themselves (see FIG. 8). This would be useful, for example, if the user only sometimes wears a light 34 with his or her loupes 32.

The cut outs 30, 102 described above are essentially U-shaped and extend from the center of the top edge downward. This shape may be advantageous in that the top opening makes it easier to seat the loupe light 34. However, as those of skill in the art will appreciate, any opening sufficient to admit a loupe light 34 will suffice in other embodiments of the invention.

Figure 7:
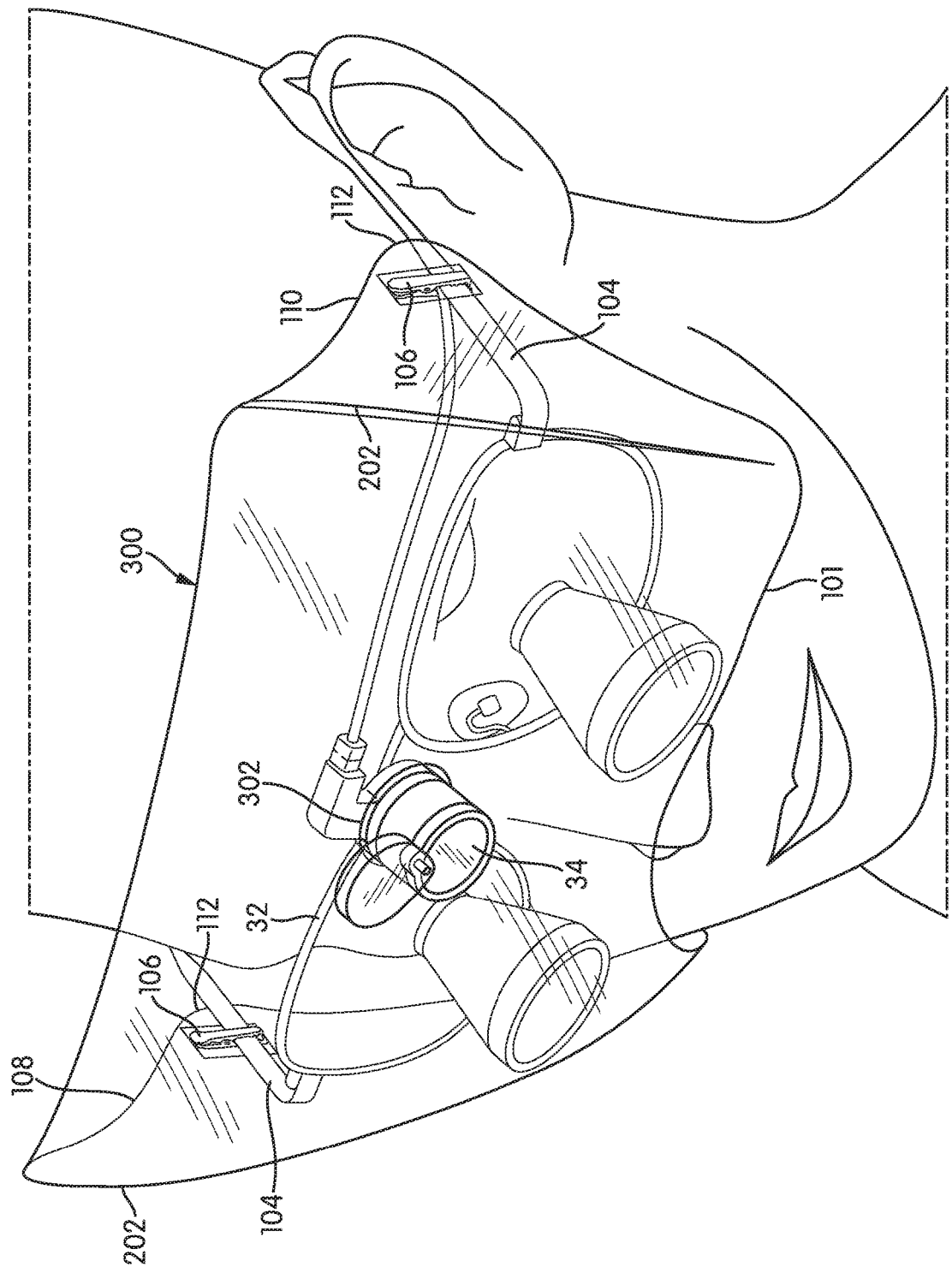
FIG. 7 is a perspective view of an attachable face shield according to a further embodiment of the invention.

FIG. 7 is a perspective view of a face shield, generally indicated at 300, according to another embodiment of the invention. The face shield 300 is similar in most all respects to the face shield 200 described above. However, the face shield 300 does not have the cut out 30, 102 of the other embodiments. Instead, an opening 302 is provided in the central portion of the face shield 300, a distance from the top edge. In the illustrated embodiment, the opening 302 is circular and is just larger than the loupe light 34 itself. The opening 302 may be, e.g., 1-3 inches in diameter, depending on the diameter of the loupe light 34. While the face shield 300 has a circular opening 302, the shape is not critical; other embodiments may use ovals and other shapes.

The face shield 300 may provide better protection for the forehead and upper areas of the face than the other face shields 100, 200 and face shield portions 14; however, seating the loupe light 34 in the opening 302 may require slightly more effort than with a cut out 30, 102.

While the invention has been described with respect to certain embodiments, the description is intended to be exemplary, rather than limiting. Modifications and changes may be made within the scope of the invention, which is defined by the appended claims.

What is claimed is:

1. A face shield, comprising:
 a sheet of a transparent, flexible material having a central portion with a top edge, a bottom edge, an inner side and an outer side;
 a right side score line extending from the top edge of the central portion towards the bottom edge;
 a left side score line extending from the top edge of the central portion towards the bottom edge;
 a right side portion extending from the right side score line away from the central portion having a tapered top edge, a tapered bottom edge and a rounded point where the tapered top edge of the right side portion and the tapered bottom edge of the right side portion meet;
 a left side portion extending from the left side score line away from the central portion having a tapered top edge, a tapered bottom edge and a rounded point where the tapered top edge of the left side portion and the tapered bottom edge of the left side portion meet;
 a right side attachment feature on an inner side of the right side portion between the tapered top edge of the right side portion and the tapered bottom edge of the right side portion;
 a left side attachment feature on an inner side of the left side portion between the tapered top edge of the left side portion and the tapered bottom edge of the left side portion; and
 a cut out horizontally centered in the central portion between the left side score line and the right side score line, the cut out having a first sidewall extending from the top edge towards the bottom edge, a second sidewall horizontally spaced from the first sidewall and extending from the top edge towards the bottom edge and a bottom extending between and joining the first sidewall and the second sidewall; and wherein the central portion of the face shield further comprises: a frangible portion sized and shaped such that the cut out is formed when the frangible portion is broken away from the central portion.

2. The face shield of claim 1 wherein the overall dimensions of the cut out are sufficient to allow passage of a loupe light.

3. The face shield of claim 1 wherein the cut out is wider toward the top edge of the central portion than along the bottom.

4. The face shield of claim 1 wherein the right side attachment feature is a clip and the left side attachment feature is a clip.

5. The face shield of claim 1 wherein the right side attachment feature is a spring loaded clip with serrated jaws and the left side attachment feature is a spring loaded clip with serrated jaws.

6. The face shield of claim 1 wherein the right side attachment feature is an adhesive tape and the left side attachment feature is an adhesive tape.

7. The face shield of claim 1 wherein the right side attachment feature is a part of a hook and loop fastener and the left side attachment feature is a part of a hook and loop fastener.

8. The face shield of claim 1 wherein on the right side portion the tapered top edge, the tapered bottom edge and the rounded point where the tapered top edge and the tapered bottom edge meet form a triangular shape and on the left side portion the tapered top edge, the tapered bottom edge and the rounded point where the tapered top edge and the tapered bottom edge meet form a triangular shape.

9. The face shield of claim 1, wherein the bottom of the cut out is rounded.

10. The face shield of claim 1 wherein a distance between the right side score line and the left side score line is 7 inches.

11. The face shield of claim 1 wherein a distance along the top edge between the right sidewall and the left sidewall is 2 inches.

12. The face shield of claim 1 wherein the cut out is deeper than it is wide.

13. The face shield of claim 1, wherein the face shield is transparent with a thickness of 0.1 mm.

14. The face shield of claim 1, wherein at least a part of the central portion includes UV filtering characteristics.

15. The face shield of claim 1, wherein the right side score line extends more than half the distance from the top edge of the central portion to the bottom edge and the left side score line extends more than half the distance from the top edge of the central portion to the bottom edge.

16. A face shield, comprising:
   a sheet of a transparent, flexible material having a central portion with a top edge, a bottom edge, an inner side and an outer side;
   a right side score line extending from the top edge of the central portion towards the bottom edge;
   a left side score line extending from the top edge of the central portion towards the bottom edge;
   a right side portion extending from the right side score line away from the central portion having a tapered top edge, a tapered bottom edge and a rounded point where the tapered top edge of the right side portion and the tapered bottom edge of the right side portion meet;
   a left side portion extending from the left side score line away from the central portion having a tapered top edge, a tapered bottom edge and a rounded point where the tapered top edge of the left side portion and the tapered bottom edge of the left side portion meet;
   a right side attachment feature on an inner side of the right side portion between the tapered top edge of the right side portion and the tapered bottom edge of the right side portion;
   a left side attachment feature on an inner side of the left side portion between the tapered top edge of the left side portion and the tapered bottom edge of the left side portion; and
   a cut out horizontally centered in the central portion, the cut out having a first sidewall extending towards the bottom edge, a second sidewall horizontally spaced from the first sidewall and extending towards the bottom edge and a bottom extending between and joining the first sidewall and the second sidewall; and wherein the central portion of the face shield further comprises: a frangible portion sized and shaped such that the cut out is formed when the frangible portion is broken away from the central portion.

17. The face shield of claim 16 wherein the overall dimensions of the cut out are sufficient to allow passage of a loupe light.

18. The face shield of claim 16 wherein the cut out is wider toward the top edge of the central portion than along the bottom.

19. The face shield of claim 16 wherein the right side attachment feature is a clip and the left side attachment feature is a clip.

20. The face shield of claim 16 wherein the right side attachment feature is an adhesive tape and the left side attachment feature is an adhesive tape.

21. The face shield of claim 16 wherein the right side attachment feature is a part of a hook and loop fastener and the left side attachment feature is a part of a hook and loop fastener.

22. The face shield of claim 16 wherein on the right side portion the tapered top edge, the tapered bottom edge and the rounded point where the tapered top edge and the tapered bottom edge meet form a triangular shape and on the left side portion the tapered top edge, the tapered bottom edge and the rounded point where the tapered top edge and the tapered bottom edge meet form a triangular shape.

23. The face shield of claim 16, wherein the bottom of the cut out is rounded.

24. The face shield of claim 16, wherein the central portion of the face shield further comprises: a frangible portion sized and shaped such that the cut out is formed when the frangible portion is broken away from the central portion.

25. The face shield of claim 16 wherein a distance between the right side score line and the left side score line is 7 inches.

26. The face shield of claim 16 wherein a distance along a top edge of the cut out between the right sidewall and the left sidewall is 2 inches.

27. The face shield of claim 16 wherein the cut out is deeper than it is wide.

28. The face shield of claim 16, wherein the face shield is transparent.

29. The face shield of claim 16, wherein the right side score line extends more than half the distance from the top edge of the central portion to the bottom edge and the left side score line extends more than half the distance from the top edge of the central portion to the bottom edge.

\* \* \* \* \*